United States Patent [19]

Lantzsch et al.

[11] Patent Number: 5,744,642

[45] Date of Patent: Apr. 28, 1998

[54] PROCESS FOR THE PREPARATION OF ALIPHATIC IMINES

[75] Inventors: Reinhard Lantzsch, Wuppertal; Werner Lindner, Köln, both of Germany

[73] Assignee: Bayer Aktiengesellschaft, Leverkusen, Germany

[21] Appl. No.: 393,762

[22] Filed: Feb. 24, 1995

[30] Foreign Application Priority Data

Mar. 3, 1994 [DE] Germany .................... 44 06 949.9

[51] Int. Cl.$^6$ .................................................. C07C 249/02
[52] U.S. Cl. .................. 564/278; 564/271; 564/276; 564/279
[58] Field of Search .................... 564/271, 276, 564/278, 279

[56] References Cited

U.S. PATENT DOCUMENTS 2,582,128  1/1952  Hurwitz ........................ 260/566

FOREIGN PATENT DOCUMENTS 0006180  1/1980  European Pat. Off. .

OTHER PUBLICATIONS

O. Meth–Cohn et al., J. Chem. Soc. Perkin Trans. 1, pp. 1173–1182 (1984).
K. Campbell, J. Am. Chem. Soc., vol. 66, pp. 82–84 (1944).
R. Layer, The Chemistry of Imines in Chem. Rev., vol. 63 pp. 489–493 (1967).
M. Fajii et al., Chemistry Letters, pp. 1493–1496 (1992).
R. Verhe et al., Tetrahedron, vol. 36, pp. 131–142 (1980).
Grant et al. "Hackh's Chemical Dictionary 4th Ed." New York, McGraw–Hill Book Co. (1969) p. 684.

Primary Examiner—Peter O'Sullivan
Attorney, Agent, or Firm—Sprung Kramer Schaefer & Briscoe

[57] ABSTRACT

The invention relates to a novel process for the preparation of aliphatic imines of the general formula (I):

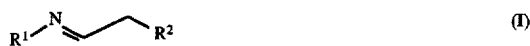

(I)

in which $R^1$ is alkyl, alkenyl, alkinyl, cycloalkyl, cycloalkylalkyl, arylalkyl or heteroarylalkyl, each of which is optionally substituted, and $R^2$ is optionally substituted alkyl and
characterized in that
amines of the general formula (II):

$$R^1\text{—}NH_2 \qquad (II)$$

in which $R^1$ is as defined above,
are reacted with aldehydes of the general formula (III):

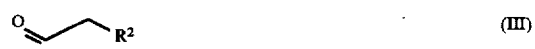

(III)

in which $R^2$ is as defined above,
in the presence of a practically water-immiscible organic solvent, at temperatures between –30° C. and +50° C.

6 Claims, No Drawings

PROCESS FOR THE PREPARATION OF ALIPHATIC IMINES

The invention relates to a novel process for the preparation of aliphatic imines which can be used as intermediates for the preparation of agrochemical or pharmaceutical active substances.

In contrast to the synthesis of aromatic imines, the preparation of aliphatic imines is known to be relatively difficult (cf. Chem. Reviews 63 (1963), 489–510, especially 493).

The only known method for the preparation of aliphatic imines—in moderate yields—is the solventless reaction of aldehydes with amines in the presence of solid potassium hydroxide (cf. J. Am. Chem. Soc. 66 (1944), 82–84; J. Chem. Soc. Perkin Trans. I 1984, 1173–1182). This method is poorly suited to industrial needs because the yield and quality of the products are unsatisfactory in many cases, the by-products cannot easily be separated off and large amounts of potassium hydroxide have to be disposed of.

It has now been found that aliphatic imines of the general formula (I):

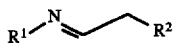
(I)

in which
R$^1$ is alkyl, alkenyl, alkinyl, cycloalkyl, cycloalkylalkyl, arylalkyl or heteroarylalkyl, each of which is optionally substituted, and
R$^2$ is optionally substituted alkyl and
are obtained in high yields and in good quality by reacting amines of the general formula (II):

(II)

in which
R$^1$ is as defined above,
with aldehydes of the general formula (III):

(III)

in which
R$^2$ is as defined above,
in the presence of a practically water-immiscible organic solvent, at temperatures between −30° C. and +50° C.

Surprisingly, the process according to the invention makes it possible to obtain the imines of the formula (I) in practically quantitative yields without the addition of a solid auxiliary substance.

The process according to the invention thus represents a valuable enrichment of the state of the art.

The invention relates preferentially to the preparation of compounds of the formula (I) in which
R$^1$ is alkyl having 1 to 6 carbon atoms which is optionally substituted by halogen or C$_1$-C$_4$-alkoxy, alkenyl or alkinyl each having 3 to 6 carbon atoms, each of which is optionally substituted by halogen, cycloalkyl or cycloalkylalkyl each having 3 to 6 carbon atoms in the cycloalkyl moieties and optionally 1 to 4 carbon atoms in the alkyl moiety, each of which is optionally substituted by halogen or C$_1$-C$_4$-alkyl, or arylalkyl having 6 or 10 carbon atoms in the aryl moiety and 1- to 4 carbon atoms in the alkyl moiety, or heteroarylalkyl having 3 to 5 carbon atoms and 1 to 3 heteroatoms—especially nitrogen, oxygen or sulphur—in the heteroaryl moiety and 1 to 4 carbon atoms in the alkyl moiety, each of which is optionally substituted by halogen, C$_1$-C$_4$-alkyl or C$_1$-C$_4$-alkoxy, and
R$^2$ is alkyl having 1 to 6 carbon atoms which is optionally substituted by halogen or C$_1$-C$_4$-alkoxy.

The invention relates especially to the preparation of compounds of the formula (I) in which
R$^1$ is methyl, ethyl, n- or i-propyl or n-, i- or s-butyl, each of which is optionally substituted by fluorine, chlorine, methoxy or ethoxy, propenyl, butenyl, propinyl or butinyl, each of which is optionally substituted by fluorine, chlorine or bromine, cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, methyl, ethyl or n- or i-propyl, or benzyl, phenylethyl, phenylpropyl, naphthylmethyl, thienylmethyl or pyridylmethyl, each of which is optionally substituted by fluorine, chlorine, bromine, methyl, ethyl, n- or i-propyl, n-, i-, s- or t-butyl, methoxy or ethoxy, and
R$^2$ is methyl, ethyl, n- or i-propyl or n-, i-, s- or t-butyl, each of which is optionally substituted by fluorine, chlorine, methoxy or ethoxy.

If, for example, methylamine and propionaldehyde are used as the starting materials, the course of the reaction in the process according to the invention can be outlined by the following equation:

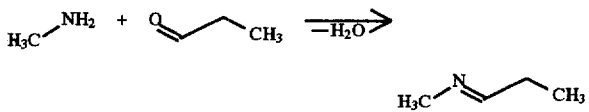

The amines to be used as starting materials in the process according to the invention for the preparation of the compounds of the general formula (I) are generally defined by the formula (II). In the formula (II), R$^1$ preferably or particularly preferably has the meaning already indicated above, in connection with the description of the compounds of the formula (I), as the preferred or particularly preferred meaning for R$^1$.

The starting materials of the formula (II) are known synthetic chemicals.

The aldehydes also to be used as starting materials in the process according to the invention are generally defined by the formula (III). In the formula (II), R$^2$ preferably or particularly preferably has the meaning already indicated above, in connection with the description of the compounds of the formula (I), as the preferred or particularly preferred meaning for R$^2$.

The starting materials of the formula (III) are known synthetic chemicals.

The process according to the invention is carried out in the presence of a practically water-immiscible organic solvent. These include especially optionally halogenated aliphatic, alicyclic or aromatic hydrocarbons such as, for example, benzine, benzene, toluene, xylene, mesitylene, chlorobenzene, dichlorobenzene, petroleum ether, pentane, hexane, heptane, cyclohexane, methylcyclohexane, dichloromethane, chloroform and carbon tetrachloride; and ethers such as, for example, diethyl ether, diisopropyl ether, t-butyl methyl ether, t-amyl methyl ether, dioxane, tetrahydrofuran and ethylene glycol dimethyl or diethyl ether. Aromatic hydrocarbons are preferred.

When the process according to the invention is carried out, the reaction temperatures can be varied within wide limits. In general, the operating temperatures are between −30° C. and +50° C., preferably between 0° C. and +30° C. and especially between 5° C. and 15° C.

The process according to the invention is generally carried out under normal pressure, but it is also possible to operate under increased or reduced pressure—generally between 0.1 bar and 10 bar.

For carrying out the process according to the invention for the preparation of the compounds of the formula (I), 0.8 to 1.2 mol, preferably 0.95 to 1.05 mol, of aldehyde of the formula (III) are generally used per mol of amine of the formula (II).

In a preferred embodiment of the process according to the invention, the starting materials of the formula (II) are mixed with the solvent and the starting materials of the formula (III) are added dropwise. The water formed in the reaction separates out as a second phase. When the separation of the water is complete, the organic phase is separated off. Traces of water can be removed in conventional manner, if necessary.

The product of the formula (I) can be isolated by distillation; however, it can also advantageously be used in solution for further reactions.

The imines of the formula (I) to be prepared by the process according to the invention can be used as intermediates for the preparation of insecticides (cf. EP-A-546418).

PREPARATORY EXAMPLE (general description):

1 mol of aldehyde of the formula (III) is added dropwise to 1 mol of amine of the formula (II) in 500 ml of toluene. The mixture is then left to stand at 5° C. to 15° C. until the separation of the water is complete. The organic phase is then separated off, dried over sodium sulphate and filtered.

The filtrate contains the product of the formula (I) in practically quantitative yield and can be used directly for further reactions.

The compounds of the formula (I) listed in Table 1 below, for example, can be prepared in the manner described above.

TABLE 1

Examples of the compounds of the formula (I) to be prepared according to the invention

| Ex. No. | R$^1$ | R$^2$ |
|---|---|---|
| 1 | CH$_3$ | CH$_3$ |
| 2 | C$_2$H$_5$ | CH$_3$ |
| 3 | C$_3$H$_7$ | CH$_3$ |
| 4 | C$_4$H$_9$ | CH$_3$ |
| 5 | C$_6$H$_5$CH$_2$ | CH$_3$ |
| 6 | C$_6$H$_5$CH$_2$ | CH$_2$OCH$_3$ |
| 7 | C$_6$H$_5$CH$_2$ | C$_2$H$_5$ |

TABLE 1-continued

Examples of the compounds of the formula (I) to be prepared according to the invention

| Ex. No. | R$^1$ | R$^2$ |
|---|---|---|
| 8 | C$_6$H$_5$CH$_2$ | C$_5$H$_{11}$ |
| 9 | C$_6$H$_5$CH$_2$ | CH$_2$C$_6$H$_5$ |

The yield and purity of the imines can be determined by further reaction, e.g. catalytic hydrogenation to secondary amines.

We claim:

1. A process for the preparation of an aliphatic imine of the formula

in which

R$^1$ is alkyl, alkenyl, alkinyl, cycloalkyl, cycloalkyl-alkyl, arylalkyl or heteroarylalkyl, each of which is optionally substituted, and R$^2$ is methyl, ethyl, n-propyl or n-butyl, optionally substituted by fluorine, chlorine, methoxy or ethoxy, which comprises reacting an amine of the formula

with an approximately equimolar amount of an aldehyde of the formula

in the presence of a practically water-immiscible organic solvent, at a temperature between −30° C. and +15° C. wherein the aldehyde is used in an amount of from 0.95 to 1.05 mol per mol of amine, the imine being isolated without further purification by distillation.

2. The process according to claim 1, wherein the reaction is effected between about 5° and 15° C.

3. The process according to claim 1, wherein R$^2$ is methyl.

4. The process according to claim 1, wherein R$^2$ is ethyl.

5. The process according to claim 1, wherein R$^2$ is n-propyl.

6. The process according to claim 1, wherein R$^2$ is n-butyl.

* * * * *